(12) United States Patent
Ishihara

(10) Patent No.: US 9,513,219 B2
(45) Date of Patent: Dec. 6, 2016

(54) FLUOROSCOPY APPARATUS AND IMAGE DISPLAY METHOD THEREFOR

(71) Applicant: OLYMPUS CORPORATION, Tokyo (JP)

(72) Inventor: Yasushige Ishihara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 502 days.

(21) Appl. No.: 14/058,907

(22) Filed: Oct. 21, 2013

(65) Prior Publication Data

US 2014/0049626 A1 Feb. 20, 2014

Related U.S. Application Data

(63) Continuation of application No. PCT/JP2012/061145, filed on Apr. 25, 2012.

(30) Foreign Application Priority Data

Apr. 28, 2011 (JP) ................................. 2011-101965

(51) Int. Cl.
| | |
|---|---|
| *G01N 21/64* | (2006.01) |
| *A61B 1/00* | (2006.01) |
| *A61B 1/04* | (2006.01) |

(52) U.S. Cl.
CPC ............. *G01N 21/64* (2013.01); *A61B 1/0005* (2013.01); *A61B 1/00009* (2013.01); *A61B 1/00096* (2013.01); *A61B 1/043* (2013.01)

(58) Field of Classification Search
CPC .................................................... G01N 21/64
See application file for complete search history.

(56) References Cited

U.S. PATENT DOCUMENTS

| | | | |
|---|---|---|---|
| 5,749,830 A | 5/1998 | Kaneko et al. | |
| 2008/0068454 A1* | 3/2008 | Hirakawa | A61B 1/00009 348/65 |
| 2010/0049058 A1 | 2/2010 | Ishihara | |

FOREIGN PATENT DOCUMENTS

| | | |
|---|---|---|
| EP | 2 412 294 A1 | 2/2012 |
| JP | 63-240826 A | 10/1988 |

(Continued)

OTHER PUBLICATIONS

International Search Report dated Jul. 17, 2012 issued in PCT/JP2012/061145.

*Primary Examiner* — Mohammed Rahaman
(74) *Attorney, Agent, or Firm* — Scully, Scott, Murphy & Presser, P.C.

(57) ABSTRACT

Provided is a fluoroscopy apparatus including illuminating portions that radiate excitation light and illumination light onto an imaging subject; a fluorescence imaging portion that acquires a fluorescence image from fluorescence emitted at the imaging subject due to the irradiation with the excitation light; a return-light imaging portion that acquires a return-light image from return light returning from the imaging subject due to the irradiation with the illumination light; a display portion that displays the acquired fluorescence image and/or the return-light image; an identifying portion that identifies a region-of-interest in the fluorescence image; an image switching portion that switches the display on the display portion so that only the return-light image is displayed thereon when the region-of-interest R is not identified, and so that the return-light image and the fluorescence image are juxtaposed and displayed on the display portion when the region-of-interest has been identified.

10 Claims, 13 Drawing Sheets

(56) References Cited

FOREIGN PATENT DOCUMENTS

| | | | |
|---|---|---|---|
| JP | 2002-345739 A | | 12/2002 |
| JP | 2006-20788 A | * | 1/2006 |
| JP | 2006-020788 A | | 1/2006 |
| JP | 2006-095166 A | | 4/2006 |
| JP | 2007-075198 A | | 3/2007 |
| JP | 2009-045148 A | | 3/2009 |
| JP | 2009-226072 A | | 10/2009 |
| WO | 2010/110117 A1 | | 9/2010 |

* cited by examiner

FLUOROSCOPY APPARATUS AND IMAGE DISPLAY METHOD THEREFOR

CROSS-REFERENCE TO RELATED APPLICATIONS

This is a continuation of International Application PCT/JP2012/061145, with an international filing date of Apr. 25, 2012, which is hereby incorporated by reference herein in its entirety. This application claims the benefit of Japanese Patent Application No. 2011-101965, the content of which is incorporated herein by reference.

TECHNICAL FIELD

The present invention relates to a fluoroscopy apparatus and an image display method therefor.

BACKGROUND ART

In the related art, there is a known endoscope apparatus in which a reflected-light image and a fluorescence image of an observation subject are acquired, one of the images is displayed in a main window on a monitor, and the other image is displayed in a subwindow (for example, see Patent Literature 1). In addition, there is also a known endoscope apparatus in which a reflected-light image and a fluorescence image are displayed in a superimposed manner (for example, see Patent Literature 2).

In the process of inserting the inserted portion of an endoscope into the body of a patient, an observer, such as a doctor or the like, performs the insertion task by mainly using the reflected-light image, and, in the process of observing the vicinity of a diseased portion, the observer observes mainly the fluorescence image.

CITATION LIST

Patent Literature

{PTL 1} Japanese Unexamined Patent Application, Publication No. 2002-345739
{PTL 2} Japanese Unexamined Patent Application, Publication No. 2007-075198

SUMMARY OF INVENTION

Solution to Problem

A first aspect of the present invention provides a fluoroscopy apparatus including an illuminating portion that radiates excitation light and illumination light onto an imaging subject; a fluorescence imaging portion that acquires a fluorescence image by capturing fluorescence emitted at the imaging subject due to the irradiation with the excitation light from the illuminating portion; a return-light imaging portion that acquires a return-light image by capturing return light returning from the imaging subject due to the irradiation with the illumination light from the illuminating portion; a display portion that displays the fluorescence image acquired by the fluorescence imaging portion and/or the return-light image acquired by the return-light imaging portion; an identifying portion that identifies, in the fluorescence image, a region that includes a gradation value that exceeds a predetermined gradation-value threshold as a region-of-interest; and an image switching portion that switches the display on the display portion so that only the return-light image is displayed thereon when the region-of-interest is not identified by the identifying portion, and so that the return-light image and the fluorescence image are juxtaposed and displayed on the display portion when the region-of-interest is identified.

In the above-described invention, the identifying portion may identify a region that includes a gradation value that exceeds the gradation-value threshold, for which an area thereof also exceeds a predetermined area threshold, as the region-of-interest.

In addition, the above-described invention may be provided with an input portion for an observer to make an input, wherein the image switching portion may switch the display on the display portion so that, when the region-of-interest is identified by the identifying portion, information about the identified region-of-interest is displayed superimposed on the return-light image, and a display prompting the observer to make an input regarding whether or not observation is necessary for the region-of-interest corresponding to the displayed information is displayed; and the image switching portion may also switch the display so that the return-light image and the fluorescence image are displayed on the display portion when an input indicating that observation is necessary is made via the input portion.

In addition, in the above-described invention, the information about the region-of-interest may be a position of the region-of-interest in the return-light image.

In addition, in the above-described invention, the information about the region-of-interest may be a position and a mean gradation value of the region-of-interest in the return-light image.

In addition, in the above-described invention, the information about the region-of-interest may be an outline of the region-of-interest in the return-light image.

In addition, in the above-described invention, when the region-of-interest is identified by the identifying portion, the image switching portion may display the return-light image and the fluorescence image at higher magnification.

In addition, in the above-described invention, the fluorescence imaging portion and the return-light imaging portion may be individually provided with a magnification-changing mechanism that changes the magnification of the acquired images; when an input indicating that observation is necessary is made via the input portion, the individual magnification-changing mechanisms may be activated to cause the fluorescence imaging portion and the return-light imaging portion to acquire a high-magnification fluorescence image and return-light image; and the image switching portion may display the acquired high-magnification fluorescence image and return-light image.

In addition, in the above-described invention, when an input indicating that observation is not necessary is made via the input portion, the image switching portion may switch to the display including only the return-light image.

In addition, the above-described invention may be provided with a storage portion that stores, when an input is made via the input portion, the return-light image displayed on the display portion when the input is made and the region-of-interest identified by the identifying portion in association with the input content, wherein, when the region-of-interest is identified by the identifying portion, the image switching portion may compare the identified region-of-interest and a return-light image corresponding to that region-of-interest with a past region-of-interest and a past return-light image stored in the storage portion, and, if there is a match therebetween, the image switching portion may show different displays in accordance with the associated input content stored in the storage portion.

In addition, the present invention provides a fluoroscopy apparatus including an illuminating portion that radiates excitation light and illumination light onto an imaging subject; a fluorescence imaging portion that acquires a fluorescence image by capturing fluorescence emitted at the imaging subject due to the irradiation with the excitation light from the illuminating portion; a return-light imaging portion that acquires a return-light image by capturing return light returning from the imaging subject due to the irradiation with the illumination light from the illuminating portion; a display portion that displays the fluorescence image acquired by the fluorescence imaging portion and/or the return-light image acquired by the return-light imaging portion; an identifying portion that identifies, in the fluorescence image, a region that includes a gradation value that exceeds a predetermined gradation-value threshold, for which an index value obtained by multiplying this gradation value by a feature quantity other than the gradation value also exceeds a predetermined index threshold, as a region-of-interest; and an image switching portion that switches the display on the display portion so that only the return-light image is displayed thereon when the region-of-interest is not identified by the identifying portion, and so that the return-light image and the fluorescence image are displayed on the display portion when the region-of-interest is identified.

The above-described invention may be provided with an input portion for an observer to make an input, wherein the image switching portion may switch the display on the display portion so that, when the region-of-interest is identified by the identifying portion, information about the identified region-of-interest is displayed in association with the return-light image, and a display prompting the observer to make an input regarding whether or not observation is necessary for the region-of-interest corresponding to the displayed information is displayed; and the image switching portion may also switch the display so that the return-light image and the fluorescence image are displayed on the display portion when an input indicating that observation is necessary is made via the input portion.

In addition, the above-described invention may be provided with an attachable/detachable component that is attached/detached to change observation conditions and that stores identification information thereof; an identification-information reading portion that reads the identification information stored in the attachable/detachable component; and a threshold storage portion that stores the identification information in association with the gradation-value threshold, wherein the identifying portion may identify the region-of-interest by using the gradation-value threshold stored in the threshold storage portion in association with the identification information of the attached attachable/detachable component.

In addition, the above-described invention may be provided with an information input portion for inputting information about a fluorescent reagent to be used, wherein the identifying portion may adjust the gradation-value threshold based on the information about the fluorescent reagent input via the information input portion, and may identify a region in which the adjusted gradation-value threshold is exceeded as the region-of-interest.

In addition, a second aspect of the present invention provides an image display method for a fluoroscopy apparatus including radiating excitation light and illumination light onto an imaging subject; acquiring a fluorescence image by capturing fluorescence emitted at the imaging subject due to the irradiation with the excitation light; acquiring a return-light image by capturing return light returning from the imaging subject due to the irradiation with the illumination light, the image display method including identifying, in the fluorescence image, a region that includes a gradation value that exceeds a predetermined gradation-value threshold as a region-of-interest; displaying only the return-light image when the region-of-interest is not identified; and juxtaposing and displaying the return-light image and the fluorescence image when the region-of-interest is identified.

DESCRIPTION OF EMBODIMENTS

A fluoroscopy apparatus 1 according to a first embodiment of the present invention will be described below with reference to the drawings.

Figure 1:
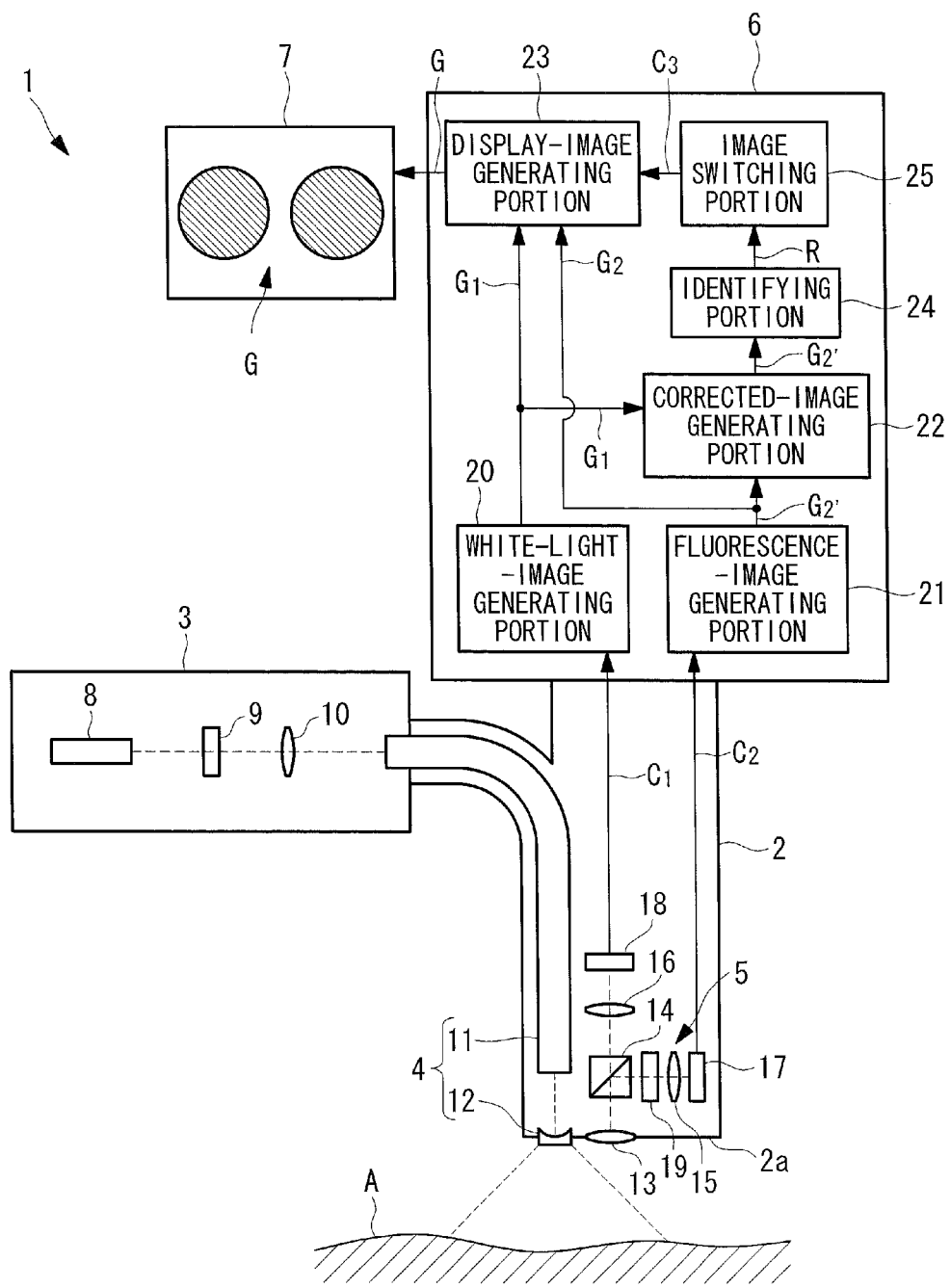
FIG. 1 is an overall configuration diagram showing a fluoroscopy apparatus according to a first embodiment of the present invention.

As shown in FIG. 1, the fluoroscopy apparatus according to this embodiment is an endoscope and is provided with a long, thin inserted portion 2 that is inserted into a body; a light source (illuminating portion) 3; an illumination unit (illuminating portion) 4 that radiates excitation light and illumination light from the light source 3 onto an imaging subject A from the distal end of the inserted portion 2; an imaging unit 5 that is provided at the distal end of the inserted portion 2 and that acquires image information about biological tissue, that is, the imaging subject A; an image processing portion 6 that is disposed at the base end of the inserted portion 2 and that processes the image information acquired by the imaging unit 5; and a monitor 7 that displays an image processed by the image processing portion 6.

The light source 3 is provided with a xenon lamp 8; a filter 9 that extracts the excitation light and the illumination light (for example, light in a wavelength band of 400 to 740 nm) from the light emitted from the xenon lamp 8; and a coupling lens 10 that focuses the excitation light and the illumination light extracted by the filter 9.

The illumination unit 4 is provided with a light-guide fiber 11 that is disposed along nearly the entire length of the inserted portion 2 in the longitudinal direction thereof and that guides the excitation light and the illumination light focused by the coupling lens 10; and an illumination optical system 12 that is provided at the distal end of the inserted portion 2, that spreads out the excitation light and the illumination light guided thereto by the light-guide fiber 11, and that radiates them onto the imaging subject A facing a distal-end surface 2a of the inserted portion 2.

The imaging unit 5 is provided with an objective lens 13 that collects light returning from a predetermined observation area of the imaging subject A; a dichroic mirror 14 that, of the light collected by the objective lens 13, reflects light having an excitation wavelength or greater (excitation light and fluorescence) and allows white light (return light) having a wavelength less than the excitation wavelength to pass therethrough; two focusing lenses 15 and 16 that respectively focus the fluorescence reflected by the dichroic mirror 14 and the white light that has passed through the dichroic mirror 14; and two imaging devices 17 and 18, like CCDs, that capture the white light and the fluorescence focused by the focusing lenses 15 and 16. The figures show an excitation light cut filter 19 that blocks the excitation light in the light reflected by the dichroic mirror 14 (allows only the light in a wavelength band of, for example, 760 to 850 nm to pass therethrough).

The image processing portion 6 is provided with a white-light-image generating portion 20 that generates a white-light image G1 based on white-light image information C1 acquired by the imaging device 18; a fluorescence-image generating portion 21 that generates a fluorescence image G2 based on fluorescence image information C2 acquired by the imaging device 17; a corrected-fluorescence-image generating portion 22 that generates a corrected fluorescence image G2' in which the fluorescence image G2 is normalized by the white-light image G1; a display-image generating portion 23 that generates a display image G to be displayed on the monitor 7 based on the white-light image G1 and/or the fluorescence image G2; an identifying portion 24 that identifies a region-of-interest R in the corrected fluorescence image G2' generated by the corrected-fluorescence-image generating portion 22; and an image switching portion 25 that switches the display image G to be generated by the display-image generating portion 23 in accordance with the region-of-interest R identified by the identifying portion 24.

Figure 2:
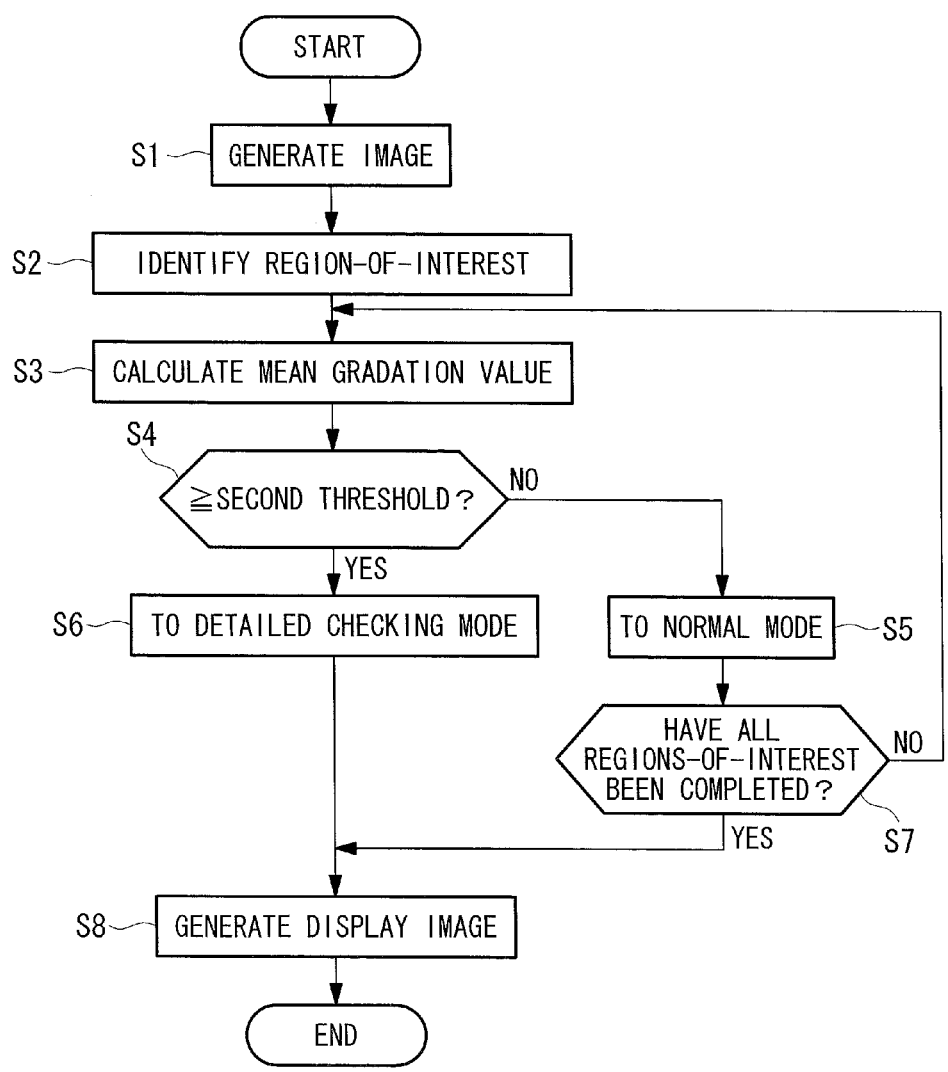
FIG. 2 is a flowchart for explaining an image display method for the fluoroscopy apparatus in FIG. 1.

FIG. 2 shows a flowchart showing the processing sequence in the image processing portion 6.

When a white-light image G1 and a fluorescence image G2 are generated by the white-light-image generating portion 20 and the fluorescence-image generating portion 21, the corrected-fluorescence-image generating portion 22 generates a corrected fluorescence image G2' by dividing the generated fluorescence image G2 by the white-light image G1 (Step S1).

By selecting pixels having gradation values equal to or greater than a first threshold (gradation-value threshold), which is set in advance, from among gradation values of individual pixels of the corrected fluorescence image G2', the identifying portion 24 identifies one or more regions that include a plurality of pixels as regions-of-interest R (Step S2).

By doing so, by using the gradation-value threshold adjusted based on the information about the fluorescent reagent, the region-of-interest can be identified with high precision even if the contrast of the fluorescence image changes due to changes in the fluorescent reagent used.

For each region-of-interest R, the image switching portion 25 receives the gradation values of the individual pixels included in the region-of-interest R identified by the identifying portion 24; calculates a mean gradation value by adding up and averaging the gradation values of the pixels included in that region-of-interest R (Step S3); and judges whether or not this mean gradation value exceeds a second threshold (Step S4).

Then, the image switching portion 25 outputs an instruction signal C3 to the display-image generating portion 23 so as to give an instruction to use a "normal mode" when the mean gradation value is less than the second threshold, and so as to give an instruction to use a "detailed checking mode" when the mean gradation value is equal to or greater than the second threshold (Steps S5 and S6). When the normal mode is selected, the mean gradation value is calculated for another region-of-interest R and the judgment is made for that value (Step S7).

Figure 3A:
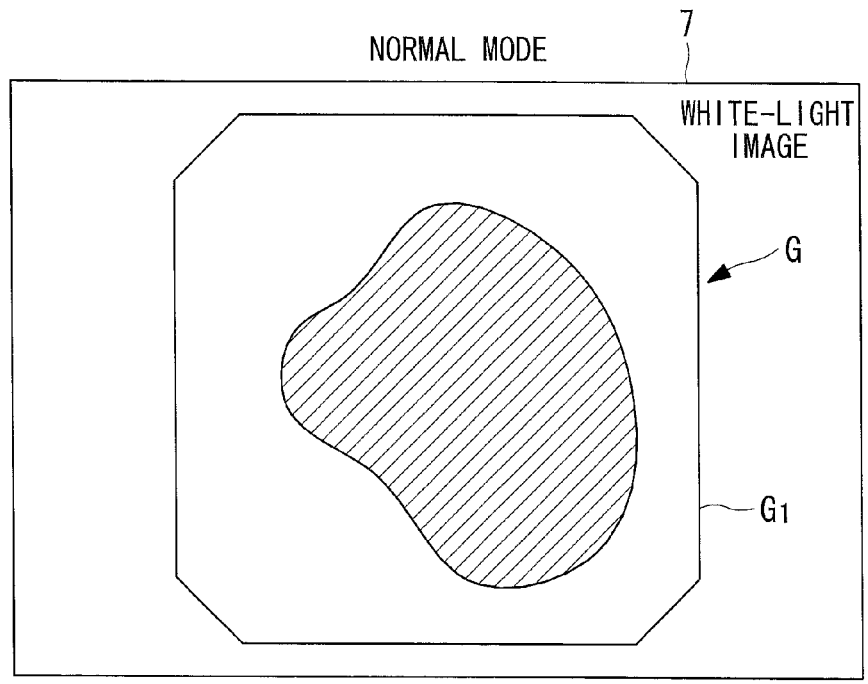
FIG. 3A is a diagram showing an example display image in a normal mode, generated by the fluoroscopy apparatus in FIG. 1.
Figure 3B:
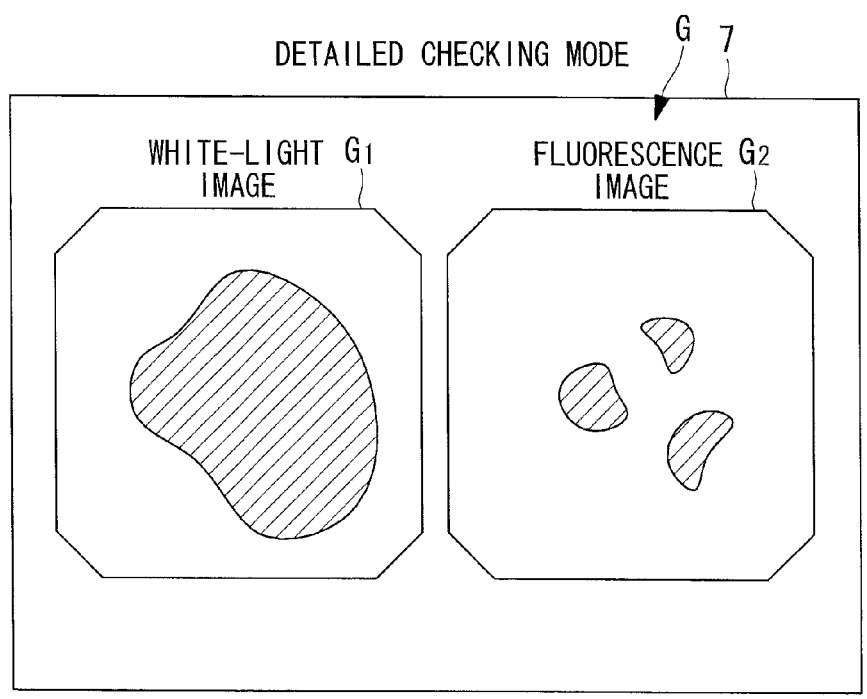
FIG. 3B is a diagram showing an example display image in a detailed checking mode, generated by the fluoroscopy apparatus in FIG. 1.

The display-image generating portion 23 receives as inputs the white-light image 01 from the white-light-image generating portion 20, the fluorescence image G2 from the fluorescence-image generating portion 21, and the instruction signal C3 from the image switching portion 25. When an instruction signal C3 instructing use of the "normal mode" is input from the image switching portion 25, the display-image generating portion 23 generates an image consisting solely of the white-light image as the display image G, as shown in FIG. 3A, and outputs it to the monitor 7. In addition, when an instruction signal C3 instructing use of the "detailed checking mode" is input, the display-image generating portion generates an image in which the white-light image G1 and the fluorescence image G2 are juxtaposed and combined as the display image G, as shown in FIG. 3B, and outputs it to the monitor 7 (Step S8).

With the thus-configured fluoroscopy apparatus 1 according to this embodiment, in a fluoroscopy apparatus in which a fluorescence image is acquired by capturing the fluorescence emitted by a fluorescent substance that is contained in the imaging subject and excited by the irradiation with the excitation light, and in which a return-light image is acquired by capturing the return light returning from the imaging subject due to the irradiation with the illumination light, a region that includes a gradation value that exceeds the gradation-value threshold is identified as the region-of-interest in the acquired fluorescence image.

Then, in a state in which the region-of-interest is not identified, only the return-light image is displayed and, when the region-of-interest is identified, the return-light image and the fluorescence image are displayed in a juxtaposed manner. Accordingly, in the state in which only the return-light image is displayed, the observer can perform observation by focusing only on the return-light image. On the other hand, when the fluorescence image is displayed, in a juxtaposed manner, in addition to the return-light image, the observer can recognize the presence of the region-of-interest and can perform the observation while checking both the return-light image and the fluorescence image.

As a result, at a stage in which there is no region to be focused on in the fluorescence image, the observer does not need to pay attention to both the return-light image and the fluorescence image, and the observer can perform observation while focusing only on the return-light image, thus making it possible to reduce the burden on the observer. In addition, when the region-of-interest is identified, by displaying the fluorescence image in a juxtaposed manner, it is possible to notify the observer about the presence of the region-of-interest, and thus, it is possible to more reliably prevent the region-of-interest from being overlooked.

In contrast, with the endoscope apparatus of Patent Literature 1, because a reflected-light image and a fluorescence image are always displayed on the same monitor, the observer must perform the task of inserting the inserted portion and searching for a diseased portion while always viewing the two images, and the burden on the observer is large. In other words, while focusing on the reflected-light image, there is a possibility of overlooking an image of a diseased portion that has appeared in the fluorescence image, and while focusing on the fluorescence image, there is a possibility of paying less attention when observing the reflected-light image.

In addition, with the endoscope apparatus of Patent Literature 2, although a superimposed reflected-light image and fluorescence image can be checked on the same window at the same time, there is a possibility in that one of the superimposed images causes a loss of clarity in the other image, or one image is hidden by the other image.

Thus, observation can be performed, while reducing the burden on an observer, without overlooking a region-of-interest and also by accurately ascertaining an observation location in an imaging subject.

The operation of the thus-configured fluoroscopy apparatus 1 according to this embodiment will be described below.

To observe biological tissue in the body of a patient, that is, the imaging subject A, by using the fluoroscopy apparatus 1 according to this embodiment, the inserted portion 2 is inserted into the body, and the distal-end surface 2a of the inserted portion 2 is disposed facing the imaging subject A. Then, the light source 3 is activated, thus emitting the excitation light and the illumination light, which are then made incident on the light-guide fiber 11 by means of the coupling lens 10. The excitation light and the illumination light that have reached the distal end of the inserted portion 2 by being guided through the light-guide fiber 11 are spread out by the illumination optical system 12 at the distal end of the inserted portion 2 and radiated onto the imaging subject A.

At the imaging subject A, a fluorescent substance contained therein is excited by the excitation light, thus emitting fluorescence, and the white light is also reflected at the surface of the imaging subject A. The fluorescence and the reflected light (white light) of the illumination light return to the distal-end surface 2a of the inserted portion 2 from an observation area, which is a portion of the imaging subject A, and are collected by the objective lens 13.

The fluorescence and the white light collected by the objective lens 13 are split by the dichroic mirror 14 in accordance with the wavelength thereof, and light that has passed through the dichroic mirror 14, for example, the white light in the wavelength band of 400 to 700 nm, is focused by the focusing lens 16 and acquired by the imaging device 18 as the white-light image information C1.

In addition, of the fluorescence and the white light collected by the objective lens 13, light reflected at the dichroic mirror 14, for example, the fluorescence including the excitation light in a wavelength band of 700 to 850 nm, is focused by the focusing lens 15 after the excitation light (for example, light having a wavelength equal to or less than 740 nm) is removed by the excitation light cut filter 19, and is acquired by the imaging device 17 as the fluorescence image information C2.

An image display method for the fluoroscopy apparatus 1 according to this embodiment will be described below.

The image information C1 and C2 acquired by the respective imaging devices 17 and 18 is transmitted to the image processing portion 6. At the image processing portion 6, the white-light image information C1 is input to the white-light-image generating portion 20, thus generating the white-light image G1. On the other hand, the fluorescence image information C2 is input to the fluorescence-image generating portion 21, thus generating the fluorescence image G2.

The generated white-light image G1 and the fluorescence image G2 are transmitted to the corrected-fluorescence-image generating portion 22, and the fluorescence image G2 is divided by the white-light image G1. By doing so, the normalized corrected fluorescence image G2' is generated.

The corrected fluorescence image G2' generated at the corrected-fluorescence-image generating portion 22 is transmitted to the identifying portion 24, where regions-of-interest R that include gradation values that are equal to or greater than the first threshold are identified, and the information thereof is transmitted to the image switching portion 25.

At the image switching portion 25, by using the information about the region-of-interest R transmitted thereto from the identifying portion 24, a mean gradation value is calculated for each region-of-interest R, and the calculated mean gradation values are compared with the second threshold. Then, if there is no region-of-interest R whose mean gradation value is equal to or greater than the second threshold, the instruction signal C3 instructing use of the "normal mode" is transmitted to the display-image generating portion 23, and a display image G including only the white-light image G1 is generated and displayed on the monitor 7.

On the other hand, at the image switching portion 25, if there is a region-of-interest R whose mean gradation value is equal to or greater than the second threshold among the regions-of-interest R transmitted thereto from the identifying portion 24, the instruction signal C3 instructing use of the "detailed checking mode" is transmitted to the display-image generating portion 23, and a display image G in which the white-light image G1 and the fluorescence image G2 are juxtaposed and combined is generated and displayed on the monitor 7.

In this way, with the fluoroscopy apparatus 1 and the image display method therefor according to this embodiment, when an observer, such as a doctor or the like, manipulates the inserted portion 2 and inserts it into the body of a patient, in a state in which the distal end of the inserted portion 2 has not reached an observation site such as a diseased portion or the like, there is no region having a high concentration of fluorescent substances in an acquired fluorescence image G2, and thus, information about a region-of-interest R is not transmitted to the image switching portion 25 from the identifying portion 24. Therefore, the image switching portion 25 transmits the instruction signal C3 instructing use of the "normal mode" to the display-image generating portion 23, and a display image G consisting solely of the white-light image G1 is displayed on the monitor 7.

Therefore, during the insertion operation in which the inserted portion 2 is inserted into the body, the observer should focus only on the white-light image G1 displayed on the monitor 7. As a result, without being distracted by a fluorescence image G2 which does not contain necessary information, the observer can focus his/her attention on the insertion task while observing the morphological features of the biological tissue in the body by using the white-light image G1, and he/she can manipulate the inserted portion 2 while accurately confirming the observation location.

On the other hand, when the task of inserting the inserted portion 2 progresses and the distal end of the inserted portion 2 reaches the vicinity of the observation site, such as a diseased portion or the like, the identifying portion 24 starts to identify regions-of-interest R that include gradation values equal to or greater than the first threshold in the fluorescence image G2. Once the regions-of-interest R are identified, the identifying portion 24 transmits information thereof, the positions of the individual pixels constituting the regions-of-interest R, and the gradation values thereof to the image switching portion 25. When the information about the regions-of-interest R is transmitted thereto, the image switching portion 25 calculates the mean gradation value for each region-of-interest R, and compares the calculated mean gradation values with the second threshold.

As a result of these comparisons, if the mean gradation values are below the second threshold, the image switching portion 25 transmits the instruction signal C3 instructing use of the "normal mode" to the display-image generating portion 23; therefore, the display image G consisting solely of the white-light image G1 is maintained on the monitor 7. In other words, even if there is a region-of-interest R in a fluorescence image G2, if the mean gradation value thereof is low, the fluorescence image G2 is not displayed. Therefore, in this case also, there is an advantage in that the observer can focus his/her attention on the insertion task while observing the morphological feature of the biological tissue in the body by using the white-light image G1 without being distracted by a fluorescence image G2 that does not contain necessary information.

Then, as a result of the comparisons at the image switching portion 25, if there is a region-of-interest R whose mean gradation value is equal to or greater than the second threshold, the instruction signal C3 instructing use of the "detailed checking mode" is transmitted to the display-image generating portion 23, a display image G in which the white-light image G1 and the fluorescence image G2 are juxtaposed is generated, and the display on the monitor 7 is switched.

In other words, when the display mode of the display image G on the monitor 7 is switched to display the fluorescence image G2, the observer can recognize that there is a region-of-interest R containing necessary information and can focus his/her attention on the fluorescence image G2 in addition to the white-light image G1.

As a result, there is an advantage in that, even in the middle of the insertion task, the observer can recognize the presence of the observation site, such as a diseased portion or the like, and thus, it is possible to more reliably prevent the problem of the insertion task being continued while overlooking the observation site.

Figure 4:
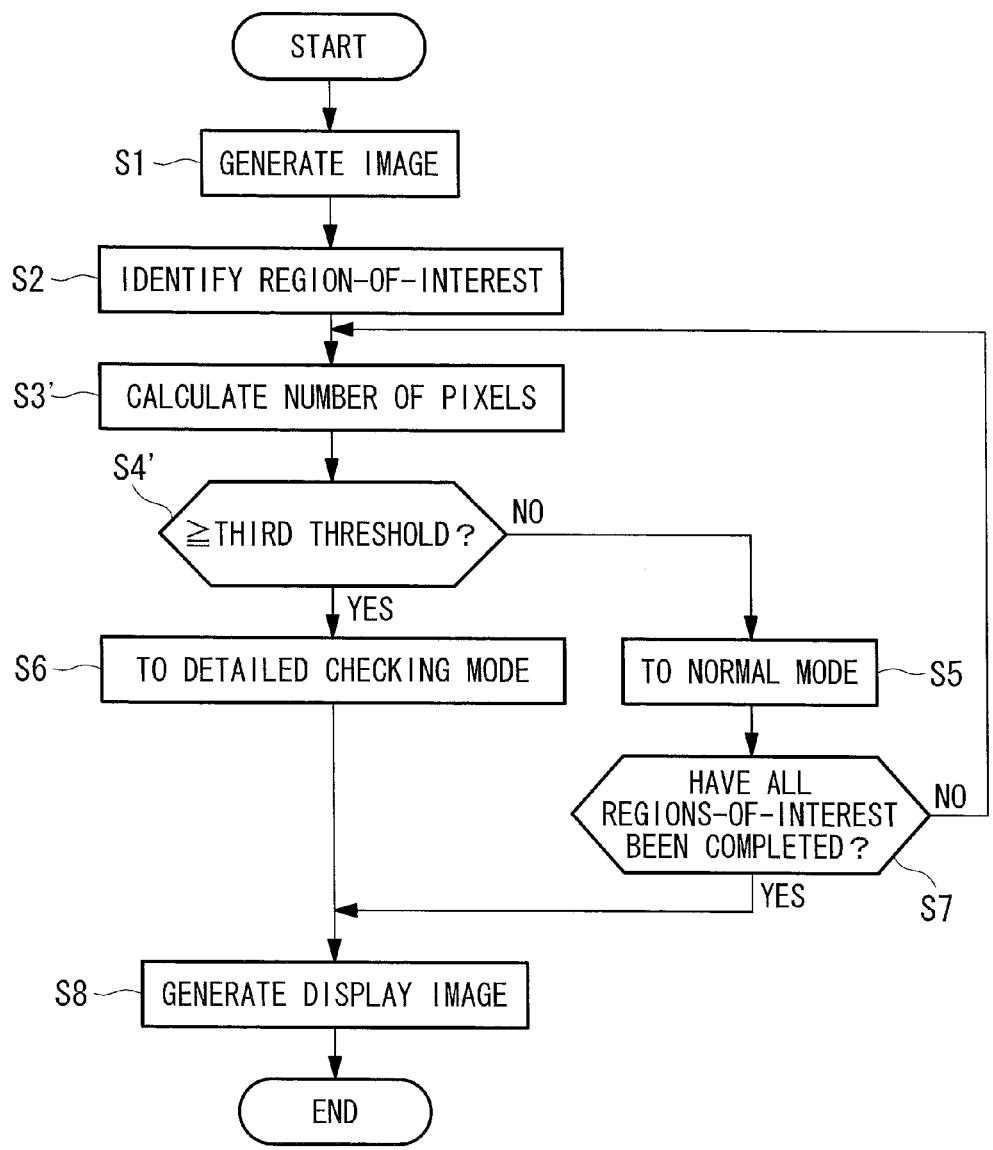
FIG. 4 is a flowchart showing a modification of the image display method in FIG. 2.

Note that, in this embodiment, the display on the monitor 7 is switched to the detailed checking mode when the mean gradation value of a region-of-interest R identified by the identifying portion 24 is equal to or greater than the second threshold; alternatively, however, the number of pixels may be calculated for each region-of-interest R for the regions-of-interest R identified as regions that include gradation values equal to or greater than the first threshold (Step S3'), and, if there is a region-of-interest R whose calculated number of pixels is equal to or greater than a third threshold (area threshold), the display on the monitor 7 may be switched to the detailed checking mode (Step S4'), as shown in FIG. 4.

By doing so, by judging whether or not it is necessary to switch the image based only on the region-of-interest R having a certain area or greater, the fluorescence image G2 will not be displayed even if the gradation value is high when the area of the region is small; therefore, it is possible to prevent the problem of the fluorescence image G2 being displayed frequently due to noise, and to considerably reduce the burden on the observer.

In other words, a region whose gradation value is high but whose area is small is prevented from being identified as the region-of-interest, and thus, it is possible to efficiently identify the region-of-interest by preventing misidentification due to noise. This makes it possible to reduce the burden on the observer due to switching of the display caused by identifying a region that is not originally intended to be focused on as the region-of-interest.

On the other hand, when it is judged whether or not it is necessary to switch the image based only on the mean gradation value, the fluorescence image G2 is displayed by treating a region-of-interest R whose gradation values are high but whose area is small also as a region where observation is necessary; therefore, it is possible to reduce the risk of overlooking the region-of-interest R.

In addition, in this embodiment, the shift to the detailed checking mode is performed when there is a region-of-interest whose mean gradation value is equal to or greater than the second threshold, among the regions-of-interest that include gradation values equal to or greater than the first threshold; however, the shift to the detailed checking mode may be performed when a region-of-interest that includes a gradation value equal to or greater than the first threshold is identified.

Next, a fluoroscopy apparatus 30 according to a second embodiment of the present invention will be described below with reference to the drawings.

In describing this embodiment, the same reference signs are assigned to the portions having common configurations with the fluoroscopy apparatus 1 according to the first embodiment described above, and the descriptions thereof will be omitted.

Figure 5:
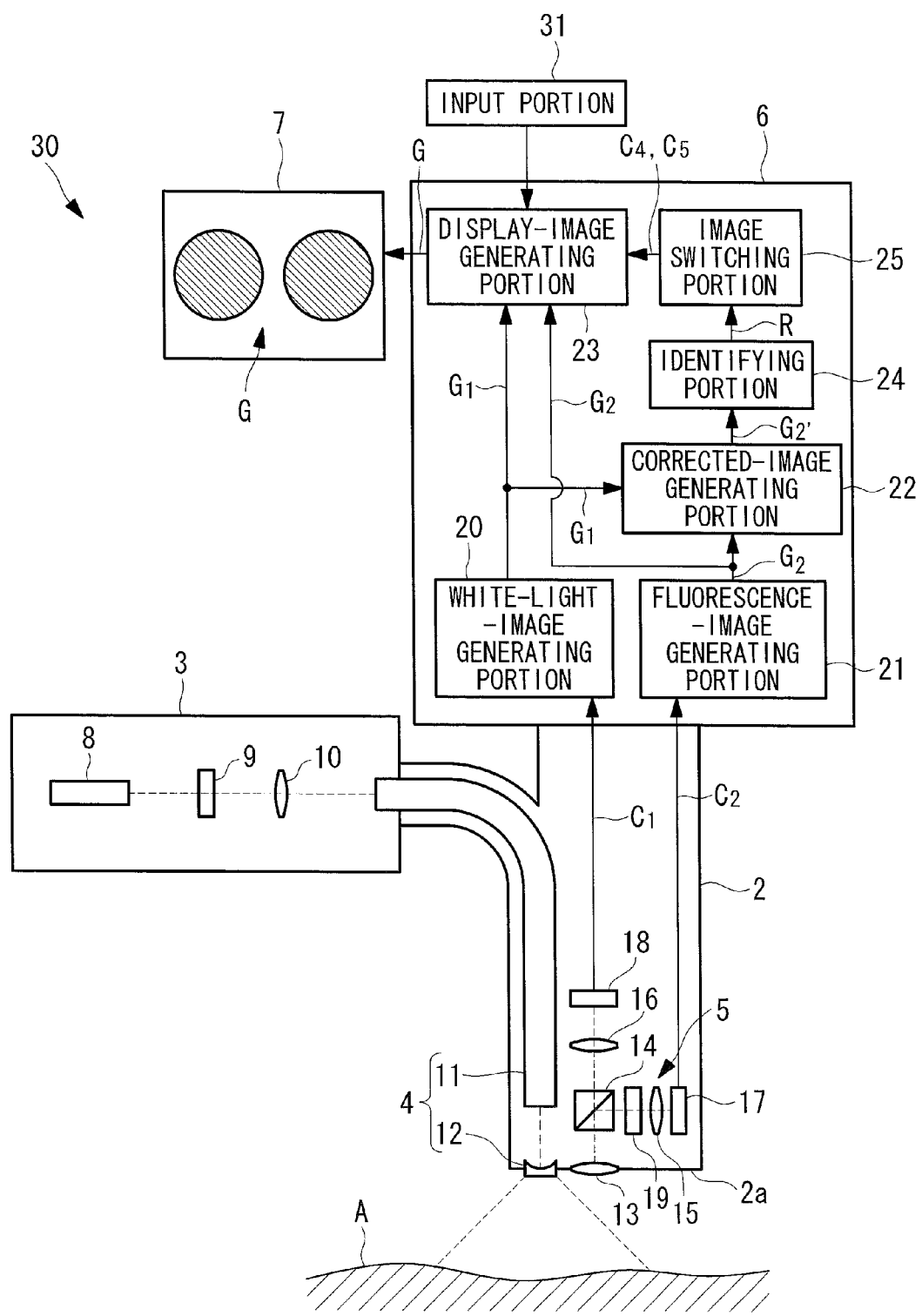
FIG. 5 is an overall configuration diagram showing a fluoroscopy apparatus according to a second embodiment of the present invention.

As shown in FIG. 5, the fluoroscopy apparatus 30 according to this embodiment differs from the fluoroscopy apparatus 1 according to the first embodiment in that an input portion 31 for the observer to make an input is included, as well as in terms of the operations of the image switching portion 25 and the display-image generating portion 23.

The input portion 31 is an arbitrary input device, for example, a pushbutton, a foot switch, a keyboard, a mouse or the like, and is connected to display-image generating portion 23.

Upon receiving the gradation values of the identified regions-of-interest R from the identifying portion 24, the image switching portion 25 calculates mean gradation values for all regions-of-interest R, and judges whether or not the mean gradation values are equal to or greater than the second threshold.

Figure 6:
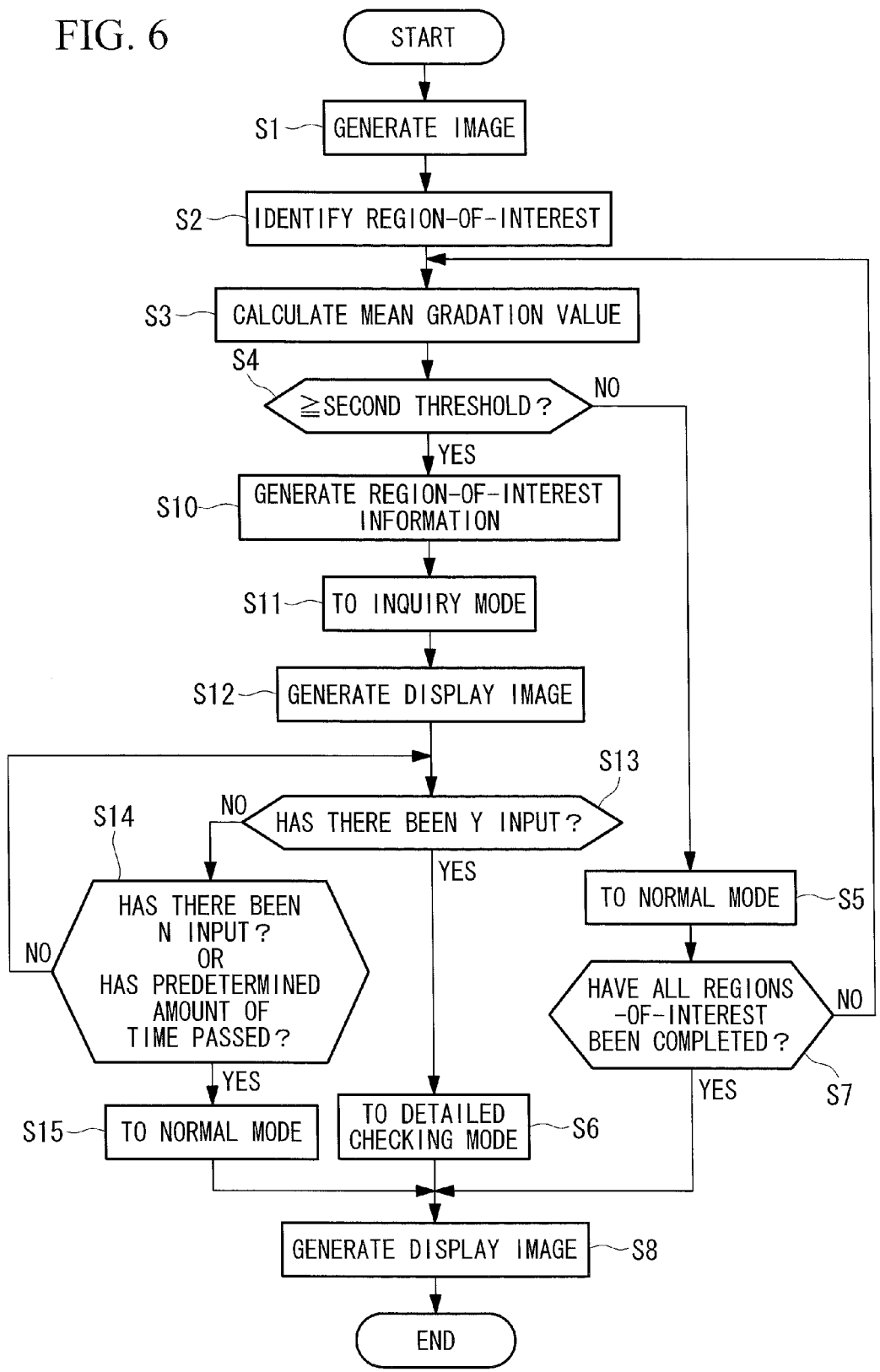
FIG. 6 is a flowchart for explaining an image display method for the fluoroscopy apparatus in FIG. 5

Furthermore, in this embodiment, as shown in FIG. 6, for the regions-of-interest R whose mean gradation values are equal to or greater than the second threshold, the image switching portion 25 generates region-of-interest information C4 (Step S10), and transmits it to the display-image generating portion 23 together with a switching instruction C5 for switching to an "inquiry mode" (Step S11).

Examples of the region-of-interest information C4 include positions and outlines of the individual regions-of-interest R, as well as center positions and maximum gradation values of the individual regions-of-interest R.

When the switching instruction C5 for the "inquiry mode" is transmitted thereto from the image switching portion 25, the display-image generating portion 23 generates an inquiry display image G in which the region-of-interest information C4, which is transmitted thereto at the same time, is superimposed on the white-light image G1 (Step S12), and outputs it to the monitor 7 together with a display that prompts the observer to make an input regarding whether or not observation is necessary (for example, "Is detailed observation necessary (Y/N)?" or the like).

In other words, when the region-of-interest is identified by the identifying portion, the information about the region-of-interest is superimposed on the return-light image. Then, a display prompting the observer to make an input regarding whether or not observation is necessary for the region-of-interest corresponding to the displayed information is displayed. While focusing on the return-light image, the observer can check the information superimposed on the return-light image with a lower burden as compared with the case in which the fluorescence image is displayed together therewith in a juxtaposed manner.

Figure 7:
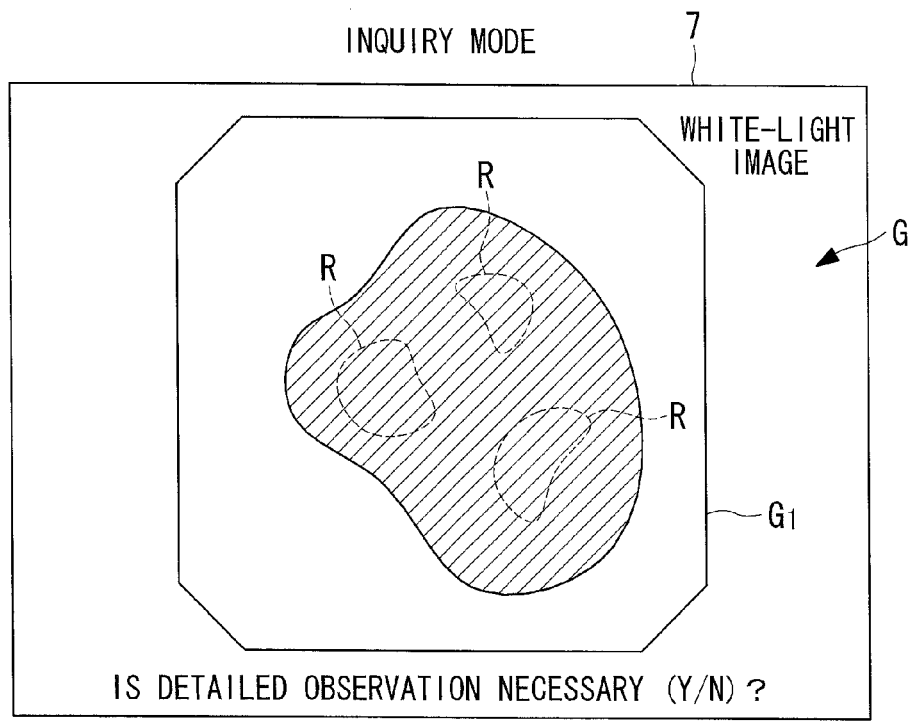
FIG. 7 is a diagram showing an example display image in an inquiry mode, generated by the fluoroscopy apparatus in FIG. 5.
Figure 8:
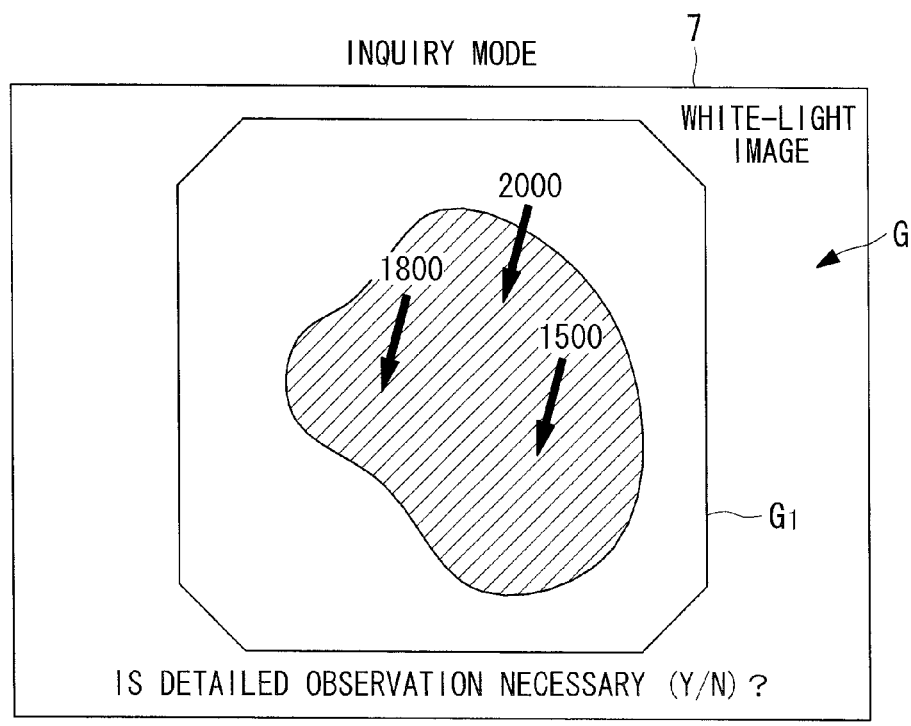
FIG. 8 is a diagram showing a modification of the example display image in FIG. 7.

FIG. 7 shows an example display image G in the inquiry mode in the case in which the position and the outline of the region-of-interest R are transmitted as the region-of-interest information C4. In addition, FIG. 8 shows an example display image G in the inquiry mode in the case in which the center position and the maximum gradation value of the region-of-interest R are transmitted as the region-of-interest information C4.

In the case in which, after checking these display images G, the observer has made an input indicating that detailed observation is necessary (Y input) by using the input portion 31 (Step S13), a shift to a detailed checking mode S6 is executed, and the display-image generating portion 23 generates a display image G in which the white-light image G1 and the fluorescence image G2 are juxtaposed (Step S8), as shown in FIG. 3B, and transmits it to the monitor 7.

By doing so, by using the information about the region-of-interest superimposed on the return-light image, it is possible to check, in a simple manner, whether or not detailed observation is necessary for the region-of-interest based on the relationship with the return-light image, and thus, observation using the return-light image and observation using the fluorescence image can be performed without imposing a burden on the observer.

In addition, in the case in which the observer has made an input indicating that detailed observation is not necessary (N input) by using the input portion 31, or when a predetermined amount of time has passed while no input is made (Step S14), a shift to a normal mode S15 is executed, and the display-image generating portion 23 generates a display image G consisting solely of the white-light image G1, as shown in FIG. 3A, and transmits it to the monitor 7.

In this way, with the fluoroscopy apparatus 30 according to this embodiment, instead of uniformly shifting to the detailed checking mode when the mean gradation value exceeds the second threshold, the shift to the detailed checking mode is executed only when the observer decides that it is necessary; therefore, there is an advantage in that the burden on the observer can be reduced even more.

In other words, distraction experienced by the observer can be eliminated by not switching to the juxtaposed display when it can be decided that a region-of-interest does not need to be observed based on the information about the region-of-interest displayed in a superimposed manner on the return-light image.

Figure 9A:
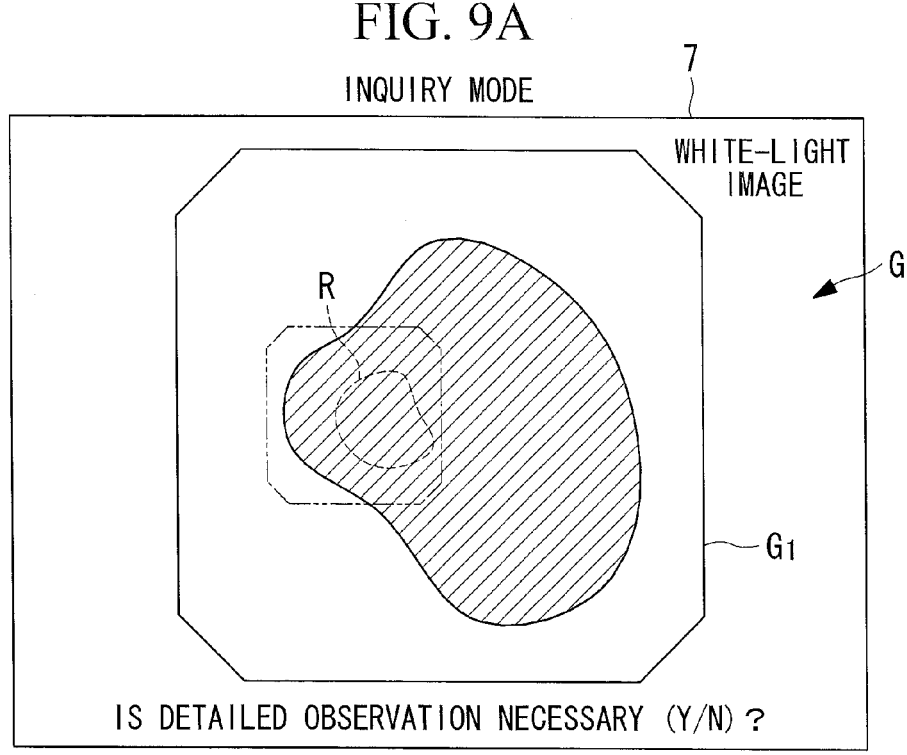
FIG. 9A is another modification of the example display image in FIG. 7, and is a diagram showing an example display image in the inquiry mode.
Figure 9B:
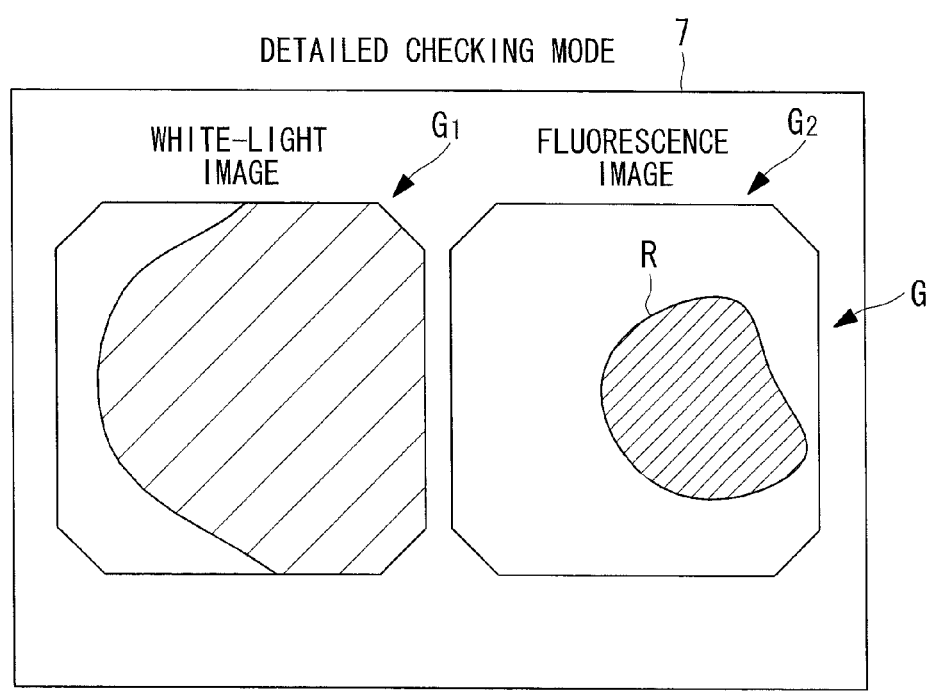
FIG. 9B is another modification of the example display image in FIG. 7, and is a diagram showing an example display image in the detailed checking mode.

Note that, in this embodiment, a display image G in which the white-light image G1 and the fluorescence image G2 are juxtaposed is generated in the detailed checking mode; alternatively, however, when shifting from the display in the inquiry mode shown in FIG. 9A to the display in the detailed checking mode shown in FIG. 9B, a display image G in which a magnified white-light image G1 (corresponding to the portion shown by the chain line in FIG. 9A) and fluorescence image G2 are juxtaposed may be generated.

Figure 10:
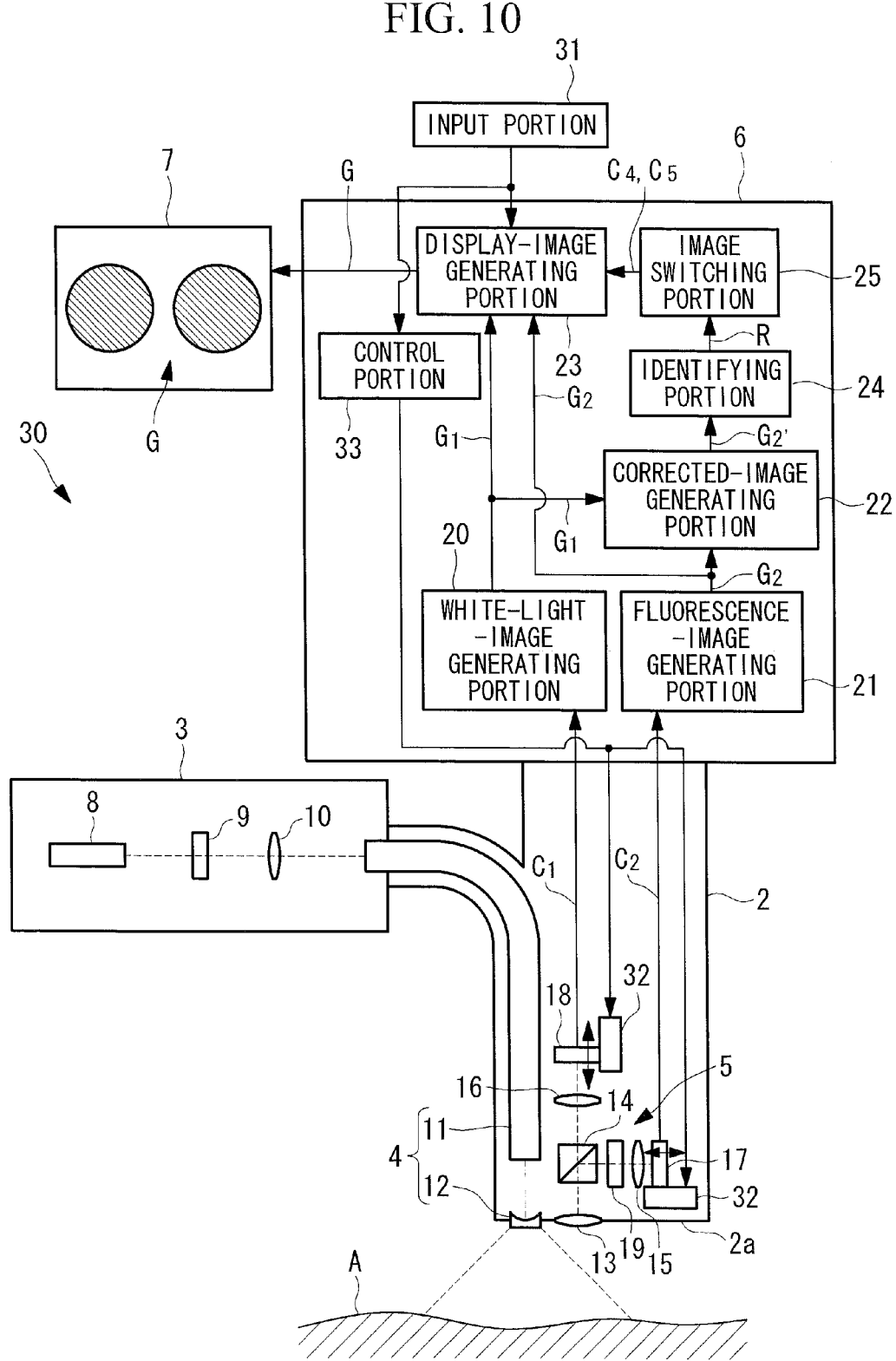
FIG. 10 is an overall configuration diagram showing a modification of the fluoroscopy apparatus in FIG. 4.

In addition, in this case, the magnified white-light image G1 and fluorescence image G2 may be generated by means of image processing, or, as shown in FIG. 10, the magnified images may be acquired by providing a magnification-changing mechanism 32 that optically changes the magnification. In the example shown in FIG. 10, the magnification-changing mechanism 32 is a sliding mechanism that moves the individual imaging devices 17 and 18 in the optical-axis direction, and is provided with a control portion 33 that causes the magnification-changing mechanism 32 to move the imaging devices 17 and 18 in the direction away from the focusing lenses 15 and 16 when the observer makes the Y input via the input portion 31. By doing so, there is an advantage in that clear magnified images can be obtained and detailed observation can be performed in the detailed checking mode.

By doing so, the region-of-interest can be observed in more detail by using the magnified return-light image and fluorescence image, and the region-of-interest can be more clearly observed by using the return-light image and fluorescence image magnified by the magnification-changing mechanism.

Next, a fluoroscopy apparatus 40 according to a third embodiment of the present invention will be described below with reference to the drawings.

In describing this embodiment, the same reference signs are assigned to the portions having common configurations with the fluoroscopy apparatus 30 according to the second embodiment described above, and the descriptions thereof will be omitted.

Figure 11:
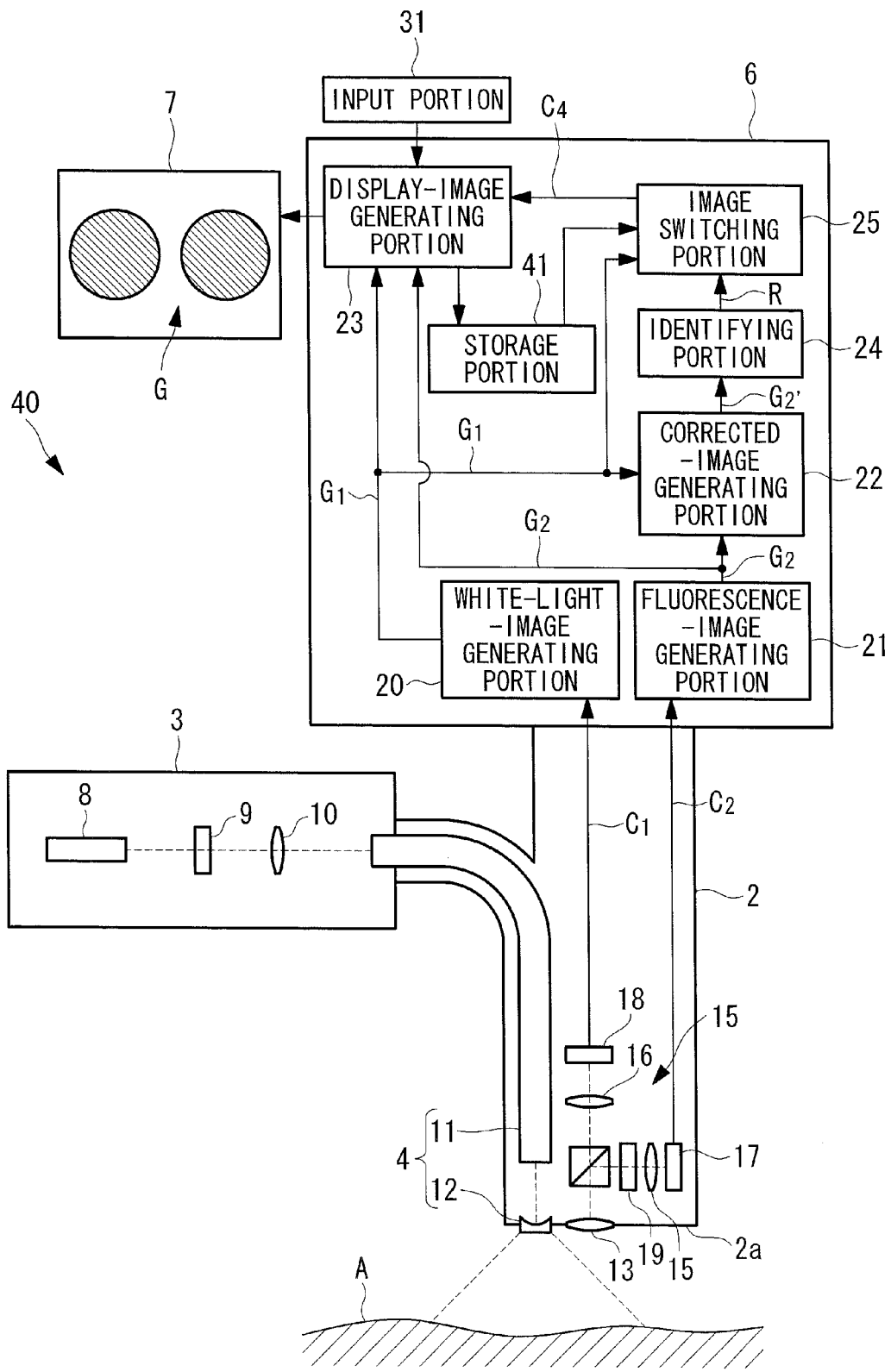
FIG. 11 is an overall configuration diagram showing a fluoroscopy apparatus according to a third embodiment of the present invention.

As shown in FIG. 11, the fluoroscopy apparatus 40 according to this embodiment is provided with a storage portion 41 that stores the displayed white-light image G1, the position and the outline of the region-of-interest R, and the input result in association with each other, when the observer makes an input via the input portion 31.

In addition, the image switching portion 25 receives the white-light image G1 from the white-light-image generating portion 20 in addition to the information about the region-of-interest R from the identifying portion 24.

Then, when the position and the outline of the region-of-interest R are transmitted from the identifying portion 24, the image switching portion 25 searches for an image that corresponds to the white-light image G1 that has been input at that point in time from the past white-light images G1 stored in the storage portion 41. Furthermore, the image switching portion 25 judges whether or not the region-of-interest R stored in association with the searched past white-light image G1 matches the region-of-interest R transmitted thereto from the identifying portion 24.

As a result of the judgment, if there is a matching past region-of-interest R, the instruction signal C4 instructing to shift to the "inquiry mode" is output to the display-image generating portion 23 together with the input result stored in association with that past region-of-interest R, and, if there is no matching past region-of-interest R, it is output together with information indicating the absence of the matching past region-of-interest R.

The display-image generating portion 23, for example, in accordance with the instruction signal C4 transmitted thereto from the image switching portion 25, generates a display image G so that, for example, the outline of the region-of-interest R is displayed in red if the region-of-interest R has received a Y input in the past, so that the outline of the region-of-interest R is displayed in blue if the region-of-interest R has received an N input, and so that the outline of the region-of-interest R is displayed in yellow if the region-of-interest R is not a region identified in the past.

By doing so, by simply viewing the color of the region-of-interest R displayed on the monitor 7, superimposed on the white-light image G1, the observer can check whether or not the region has already been judged in the past and what judgment result was given at that time. Therefore, for the region-of-interest R that has been identified even once in the past (indicated in red and blue), the observer can avoid redundant observation by making an N input via the input portion 31, and thus, he/she can efficiently observe only the region-of-interest R that has never been identified (indicated in yellow).

In other words, it is possible to make the observer recognize a region-of-interest that has been observed in the past, it is possible to choose not to use the juxtaposed display when reobservation is not necessary, and redundant detailed observation is prevented, thus enhancing the efficiency of observation.

In addition, for the region-of-interest R that has been identified in the past, the observer can easily decide whether to make a Y input to reobserve a region-of-interest R for which the input result at that time was a Y input (indicated in red), or to make an N input to avoid redundant observation for a region-of-interest R for which the input result at that time was an N input (indicated in blue).

Note that, in this embodiment, an example in which the outline of the region-of-interest R is displayed as the display in the inquiry mode has been described; alternatively, however, the position of the region-of-interest R may be displayed by using an arrow, or the fluorescence image G2 showing the region-of-interest R itself may be semi-transparently superimposed on the white-light image G1. In addition, the past input results or the like are distinguished by using different colors for the outlines of the region-of-interest R; alternatively, however, the distinction may be made by a method based on letters, etc. Also, for the region-of-interest R that has been identified in the past and for which an N input has already been made, the display in the normal mode may be continued without shifting to the inquiry mode.

Next, a fluoroscopy apparatus 50 according to a fourth embodiment of the present invention will be described below with reference to the drawings.

In describing this embodiment, the same reference signs are assigned to the portions having common configurations with the fluoroscopy apparatus 1 according to the first embodiment described above, and the descriptions thereof will be omitted.

Figure 12:
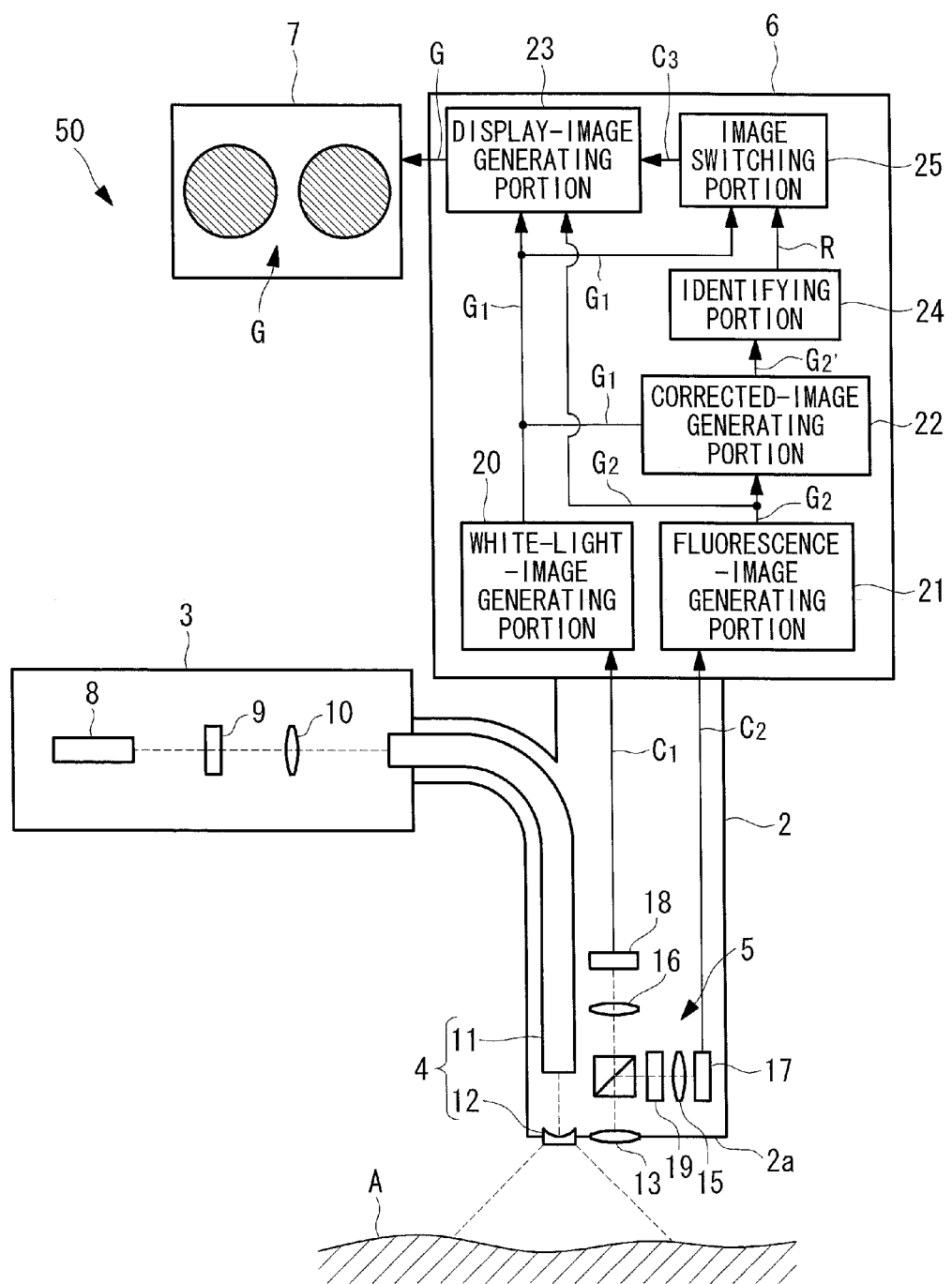
FIG. 12 is an overall configuration diagram showing a fluoroscopy apparatus according to a fourth embodiment of the present invention.

As shown in FIG. 12, the fluoroscopy apparatus 50 according to this embodiment differs in that the display is switched when an index value is equal to or greater than a fourth threshold (index threshold) as opposed to the fluoroscopy apparatus 1 according to the first embodiment in which the display is switched when the region-of-interest R identified by the identifying portion 24 has a mean gradation value equal to or greater than the second threshold.

As an index value INDEX, for example, a value calculated by multiplying a mean gradation value MF of a region-of-interest R identified by the identifying portion 24 by a mean value MR of the intensity of red in a corresponding region, which corresponds to that region-of-interest R, in the white-light image G1 is used.

$$INDEX = M_F \times M_R$$

Accordingly, the white-light image G1 generated at the white-light-image generating portion 20 is input to the image switching portion 25. When the region-of-interest R is identified by the identifying portion 24, the image switching portion 25 identifies a corresponding region, which corresponds to the region-of-interest R, in the white-light image G1 that has been transmitted thereto at that point in time, and also calculates the mean value MR of the intensity of red in that corresponding region.

Furthermore, the image switching portion 25 calculates the index value INDEX by using the above expression, and, when it is equal to or greater than the fourth threshold set in advance, transmits the instruction signal C3 instructing use of the "detailed checking mode" to the display-image generating portion 23.

In this way, with the fluoroscopy apparatus 50 according to this embodiment, the display on the monitor 7 is switched to the detailed checking mode when there is a region in which the intensity of the red is equal to or greater than the fourth threshold, in addition to the gradation value being equal to or greater than the first threshold.

When the fluoroscopy apparatus 50 is an endoscope, a high fluorescence intensity in a fluorescence image G2 indicates that there is a large amount of a fluorescent substance that tends to accumulate at a diseased portion, and a high red intensity in a white-light image G1 indicates a high blood-vessel density in that region. Because a high level of angiogenesis occurs in a tumor portion, such as cancer or the like, the blood-vessel density thereof is higher in many cases.

Therefore, there is an advantage in that, by making decision to switch the display based on the index value INDEX, a diseased portion, a tumor portion in particular, can be detected more precisely as compared with a case in which the decision is made based only on the gradation value of the fluorescence, and thus, the observer can be prompted to pay greater attention.

In other words, by identifying the region-of-interest by using the index value, the region-of-interest can be identified by taking into account a condition that another feature quantity is high, in addition to the condition that the fluorescence image has a high gradation value, and a region-of-interest where the observer needs to make detailed observation can be detected with high precision, thus reducing the burden on the observer.

Note that, in this embodiment, the index value is calculated by multiplying the mean gradation value MF of the region-of-interest R by the mean value MR of the intensity of red in the corresponding region, which corresponds to that region-of-interest R, in the white-light image G1; however, the method is not limited to multiplication, and a value obtained by adding up these values or a value obtained by adding them after multiplying them by weight coefficients may be used.

In other words, examples of a feature quantity other than the gradation value include the intensity of red in a region of the return-light image corresponding to the region that includes a gradation value that exceeds the gradation-value threshold. By doing so, for example, when observing tissue including a diseased portion, serving as the imaging subject, among regions that have high fluorescence intensity and that are suspected to be diseased portions, a region that has high red intensity and a high level of angiogenesis can be detected, with high precision, as a region having a high risk of being a tumor or the like. The burden on the observer is reduced as compared with the case in which regions having high fluorescence intensity are simply observed one by one in detail.

Next, a fluoroscopy apparatus 60 according to a fifth embodiment of the present invention will be described below with reference to the drawings.

In describing this embodiment, the same reference signs are assigned to the portions having common configurations with the fluoroscopy apparatus 1 according to the first embodiment described above, and the descriptions thereof will be omitted.

Figure 13:
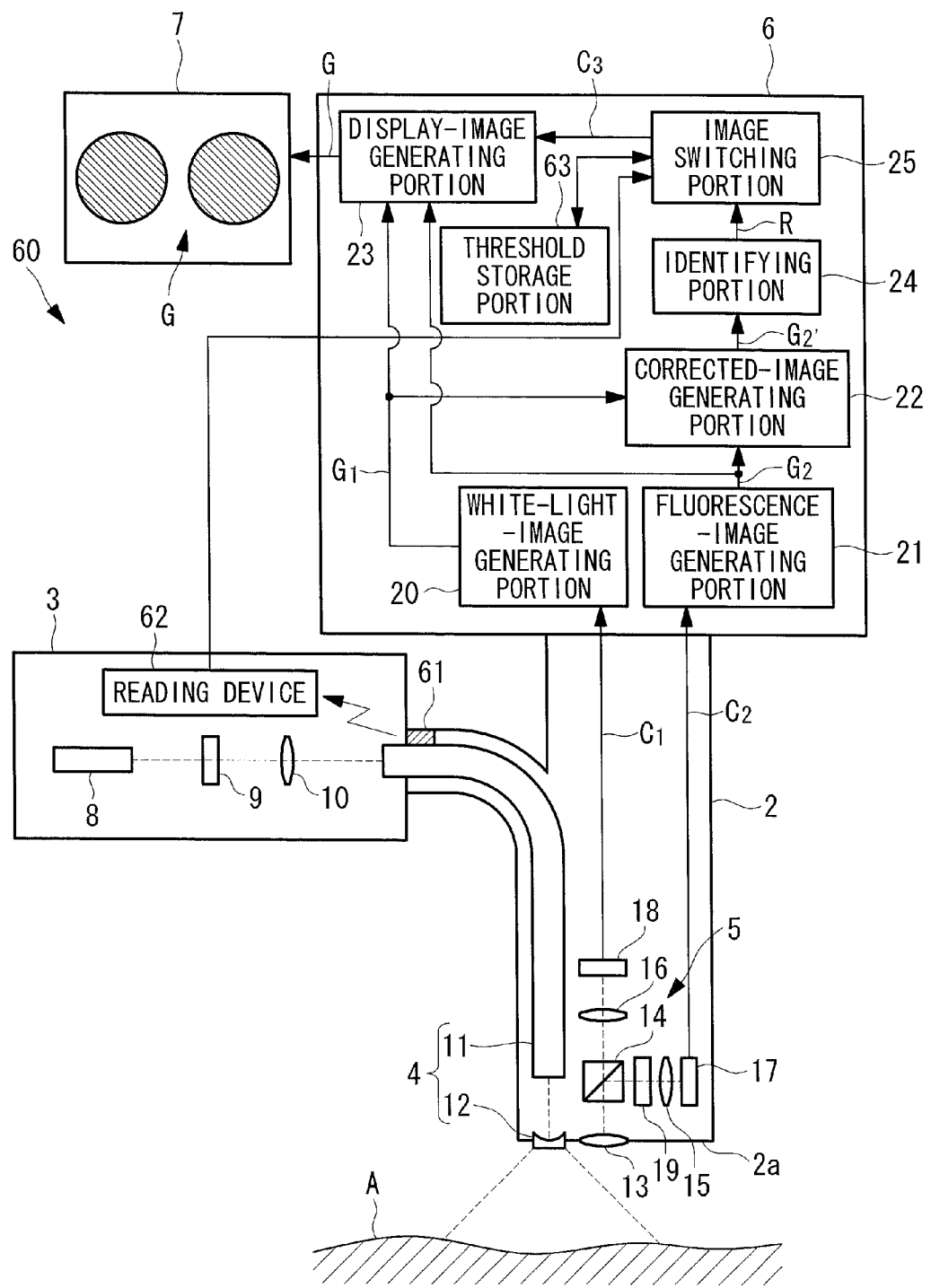
FIG. 13 is an overall configuration diagram showing a fluoroscopy apparatus according to a fifth embodiment of the present invention.

As shown in FIG. 13, the fluoroscopy apparatus 60 according to this embodiment is provided with an inserted portion (attachable/detachable component) 2 that can be attached to and detached from the light source 3 and the image processing portion 6 so that it can be exchanged in accordance with a portion serving as the observation subject. The inserted portion 2 is provided with an IC chip 61 that stores identification information of the inserted portion 2.

In addition, a reading device 62 that reads the identification information in the IC chip 61 is provided in the light source 3 to which the inserted portion 2 is attached.

By doing so, when the attachable/detachable component is attached/detached in order to change the observation conditions, the region-of-interest can be identified with high precision by using an appropriate gradation-value threshold for the attachable/detachable component, even if the sensitivity thereof changes due to the optical performance of and individual variations among attachable/detachable components.

Furthermore, the image processing portion 6 is provided with a threshold storage portion 63 that stores the identification information and thresholds in association with each other and that is connected to the identifying portion 24.

Once the inserted portion 2 is attached, the identification information in the IC chip 61 provided in this inserted portion 2 is read by the reading device 62 and is transmitted to the image processing portion 6.

At the image processing portion 6, a threshold corresponding to the identification information transmitted thereto is read out from the threshold storage portion 63 and is used as the second threshold or the third threshold for switching the display based on the region-of-interest R identified by the identifying portion 24. For example, when the fluoroscopy apparatus 60 is an endoscope, different second thresholds are used depending on whether the inserted portion 2 to be attached to the light source 3 has a small diameter or a large diameter.

Specifically, with an inserted portion 2 having a small diameter, because the illumination light level will be relatively low compared with that of a general-purpose inserted portion 2 having a large diameter, the intensity of the acquired fluorescence will also be low. Therefore, the thresholds are set in the threshold storage portion 63 so that the second threshold will be lower for the inserted portion 2 having a small diameter than for the inserted portion 2 having a large diameter.

In addition, a lesion (polyp) or the like in the large intestine is relatively large as compared with a lesion (squamous cell carcinoma) or the like in the esophagus. Therefore, the thresholds are set in the threshold storage portion 63 so that the third threshold will be lower for the case of an inserted portion 2 designed for the large intestine as compared with the case of an inserted portion 2 designed for the esophagus.

With the fluoroscopy apparatus 60 according to this embodiment, when the inserted portions 2 are exchanged, an appropriate threshold for the exchanged inserted portion 2 is read out from the threshold storage portion 63 and set; therefore, regardless of the type of the attached inserted portion 2, the display can be appropriately and automatically switched.

Figure 14:
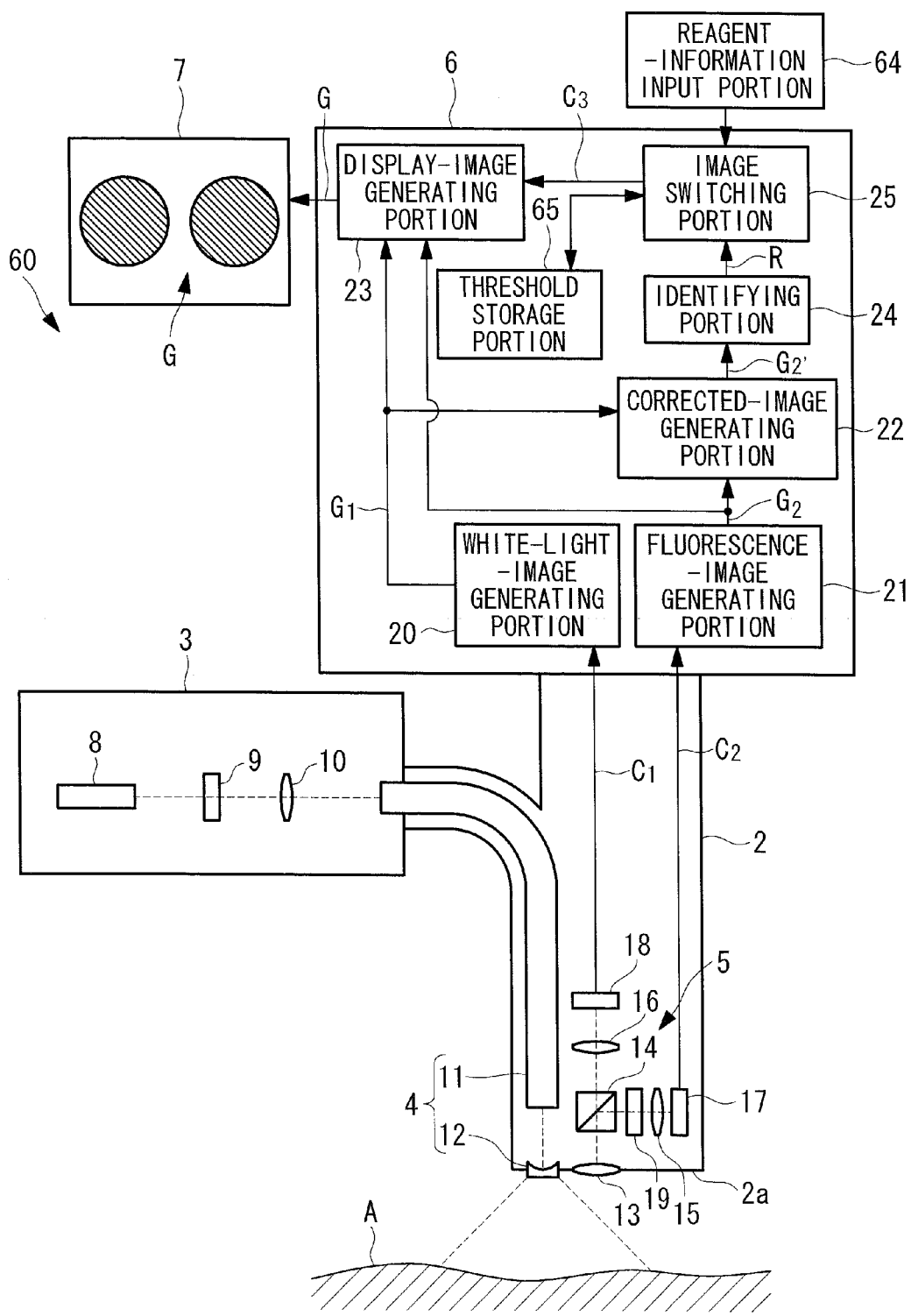
FIG. 14 is an overall configuration diagram showing a modification of the fluoroscopy apparatus in FIG. 13.

Note that, in this embodiment, an appropriate threshold is selected in accordance with the type of an attachable/detachable component like the inserted portion 2; alternatively, however, an appropriate threshold may be selected in accordance with the type of a fluorescent reagent used. In this case, as shown in FIG. 14, a reagent-information input portion 64 for inputting the type of the fluorescent reagent should be connected to the image switching portion 25, and a threshold storage portion 65 that stores the types of fluorescent reagents and the thresholds in association with each other should also be connected to the image switching portion 25.

For example, the types of the fluorescent reagent and the thresholds should be stored in association with each other so that, in the case of a fluorescent reagent whose fluorescence intensity is high, a high second threshold is set, and, in the case of a fluorescent reagent whose fluorescence intensity is low, a low second threshold is set.

By doing so, when the type of reagent fluorescence is input via the reagent-information input portion 64, the image switching portion 25 searches the threshold storage portion 65 by using the type of reagent fluorescence that has been input, and retrieves a corresponding threshold, and thus, regardless of the type of fluorescent reagent, an appropriate decision can be made about whether to use the "detailed checking mode" or to use the "normal mode".

REFERENCE SIGNS LIST

A imaging subject
G1 white-light image (return-light image)
G2 fluorescence image
R region-of-interest
S2 step of identifying a region-of-interest
S5 step of switching to normal mode
S6 step of switching to detailed checking mode
1, 30, 40, 50, 60 fluoroscopy apparatus
2 inserted portion (attachable/detachable component)
3 light source (illuminating portion)
4 illumination unit (illuminating portion)
7 monitor (display portion)
20 white-light-image generating portion (return-light imaging portion)
21 fluorescence-image generating portion (fluorescence imaging portion)
24 identifying portion
25 image switching portion
31 input portion 32 magnification-changing mechanism
41 storage portion
61 IC chip (identification information)
62 reading device (identification-information reading portion)
63 threshold storage portion
64 reagent-information input portion (information input portion)

The invention claimed is:

1. A fluoroscopy apparatus comprising:
a light source configured to radiate excitation light and illumination light onto an imaging subject;
a fluorescence image sensor configured to acquire a fluorescence image by capturing fluorescence emitted at the imaging subject due to the irradiation with the excitation light from the light source;
a return-light image sensor configured to acquire a return-light image by capturing return light returning from the imaging subject due to the irradiation with the illumination light from the light source;
a display configured to display the fluorescence image acquired by the fluorescence image sensor and/or the return-light image acquired by the return-light image sensor; and
a processor comprising hardware, wherein the processor is configured to:
identify, in the fluorescence image, a region that includes a gradation value that exceeds a predetermined gradation-value threshold as a region-of-interest; and
switch the display on the display so that only the return-light image is displayed thereon in response to the region-of-interest being not identified, and so that the return-light image and the fluorescence image are juxtaposed and displayed on the display in response to the region-of-interest being identified, and
wherein the processor is configured to switch the display on the display so that, in response to the region-of-interest being identified, information about the identified region-of-interest is displayed superimposed on the return-light image, and to control the display to display a prompt to an observer to make an input via an input device regarding whether or not observation is necessary for the region-of-interest corresponding to the displayed information, and
wherein the processor is further configured to switch the display on the display so that the return-light image and the fluorescence image are displayed on the display in response to an input indicating that observation is necessary made via the input device.

2. The fluoroscopy apparatus according to claim 1, further comprising:
a storage configured to store, in response to an input made via the input device, the return-light image displayed on the display in response to the input made and the region-of-interest being identified in association with the input content,
wherein, in response to the region-of-interest being identified, the processor is configured to compare the identified region-of-interest and a return-light image corresponding to that region-of-interest with a past region-of-interest and a past return-light image stored in the storage portion, and, if there is a match therebetween, the processor is configured to show different displays in accordance with the associated input content stored in the storage.

3. The fluoroscopy apparatus according to claim 1,
wherein the information about the region-of-interest is a position of the region-of-interest in the return-light image.

4. The fluoroscopy apparatus according to claim 1,
wherein the information about the region-of-interest is a position and a mean gradation value of the region-of-interest in the return-light image.

5. The fluoroscopy apparatus according to claim 1,
wherein the information about the region-of-interest is an outline of the region-of-interest in the return-light image.

6. The fluoroscopy apparatus according to claim 1,
wherein, in response to the region-of-interest being identified, the processor is configured to control the display to display the return-light image and the fluorescence image at higher magnification.

7. The fluoroscopy apparatus according to claim 1, further comprising:
optical elements individually provided to the fluorescence image sensor and the return-light image sensor, wherein the optical elements are configured to change the magnification of the acquired florescence image and the acquired return-light image,
wherein, in response to an input indicating that observation is necessary made via the input device, the processor is configured to:
activate the optical elements to cause the fluorescence image sensor and the return-light image sensor to acquire a high-magnification fluorescence image and return-light image; and
control the display to display the acquired high-magnification fluorescence image and return-light image.

8. The fluoroscopy apparatus according to claim 1,
wherein, in response to an input indicating that observation is not necessary made via the input device, the processor is configured to switch to the display including only the return-light image.

9. A fluoroscopy apparatus comprising:
a light source configured to radiate excitation light and illumination light onto an imaging subject;
a fluorescence image sensor configured to acquire a fluorescence image by capturing fluorescence emitted at the imaging subject due to the irradiation with the excitation light from the light source;
a return-light image sensor configured to acquire a return-light image by capturing return light returning from the imaging subject due to the irradiation with the illumination light from the light source;
a display configured to display the fluorescence image acquired by the fluorescence image sensor and/or the return-light image acquired by the return-light image sensor; and
a processor comprising hardware, wherein the processor is configured to:
identify, in the fluorescence image, a region that includes a gradation value that exceeds a predetermined gradation-value threshold, for which an index value obtained by multiplying this gradation value by a feature quantity other than the gradation value also exceeds a predetermined index threshold, as a region-of-interest; and
switch the display on the display portion so that only the return-light image is displayed thereon in response to the region-of-interest being not identified, and so that the return-light image and the fluorescence image are displayed on the display in response to the region-of-interest being identified; and wherein the processor is configured to switch the display on the display so that, in response to the region-of-interest being identified by the identifying portion, information about the identified region-of-interest is displayed in association with the return-light image, and to control the display to display a prompt to an observer to make an input via an input device regarding whether or not observation is necessary for the region-of-interest corresponding to the displayed information, and wherein the processor is further configured to switch the display on the display so that the return-light image and the fluorescence image are displayed on the display in response to an input indicating that observation is necessary made via the input device.

10. An image display method comprising:

radiating excitation light and illumination light onto an imaging subject;

acquiring a fluorescence image by capturing fluorescence emitted at the imaging subject due to the irradiation with the excitation light;

acquiring a return-light image by capturing return light returning from the imaging subject due to the irradiation with the illumination light;

identifying, in the fluorescence image, a region that includes a gradation value that exceeds a predetermined gradation-value threshold as a region-of-interest;

displaying, in response to the region-of-interest being not identified, only the return-light image on the display portion;

displaying, in response to the region-of-interest being identified, information about the identified region-of-interest by superimposing it on the return-light image and a display prompting an observer to make an input regarding whether or not observation is necessary for the region-of-interest corresponding to the displayed information; and juxtaposing and displaying the return-light image and the fluorescence image in response to an input indicating that observation is necessary.

* * * * *